United States Patent [19]

Steele et al.

[11] Patent Number: 5,357,112
[45] Date of Patent: Oct. 18, 1994

[54] METHOD FOR DETERMINING THE PRESENCE OF KNOTS OR VOIDS IN WOOD

[75] Inventors: Philip H. Steele, Starkville, Miss.; Michael Hittmeier, Alpharetta, Ga.

[73] Assignee: Mississippi State University: Forest Products Laboratory, Mississippi State, Miss.

[21] Appl. No.: 90,932

[22] Filed: Jul. 14, 1993

[51] Int. Cl.$^5$ .............. G01N 21/01; G01N 25/72
[52] U.S. Cl. ............... 250/340; 250/330; 250/358.1; 250/359.1
[58] Field of Search ............... 250/330, 334, 340, 341, 250/358.1, 359.1, 572; 356/430, 431, 237; 374/124; 83/365; 209/517, 518; 144/380

[56] References Cited

U.S. PATENT DOCUMENTS

| | | | |
|---|---|---|---|
| 3,760,667 | 9/1973 | Maxey et al. | 83/365 X |
| 3,976,384 | 8/1976 | Matthews et al. | 83/365 X |
| 4,764,017 | 8/1988 | Hiruonen | 356/237 X |
| 4,827,142 | 5/1988 | Hatje | 356/431 X |
| 4,854,724 | 8/1989 | Adams et al. | 374/124 X |
| 4,879,752 | 11/1989 | Aune et al. | 356/237 X |
| 4,886,370 | 12/1989 | Koshihara et al. | 258/330 X |
| 4,899,356 | 2/1990 | Berry et al. | 378/51 X |

FOREIGN PATENT DOCUMENTS

| | | | |
|---|---|---|---|
| 57-24811 | 2/1982 | Japan | 250/330 |
| 2-22547 | 1/1990 | Japan | 250/330 |

Primary Examiner—Constantine Hannaher
Assistant Examiner—Edward J. Glick
Attorney, Agent, or Firm—Oblon, Spivak, McClelland, Maier & Neustadt

[57] ABSTRACT

A method for determining the presence of knots and/or voids in lumber surfaces by uniformly heating the wood and then submitting the wood to an infrared camera, providing a thermal image of the surface of the wood. Knots and voids heat differently from the remaining wood areas, the differential heating being observed by the inspection of the thermal image, or more preferably by conversion of the image to a digital signal which is communicated to a frame grabber and data processor, permitting frame-by-frame inspection of the heat distribution on the surface of the wood. Locations of differential heating corresponding to knots and voids are detected, and can be communicated to subsequent processing devices, to either exclude all or some of the defect areas, or control the use to which the defect-bearing wood is put.

6 Claims, 1 Drawing Sheet

METHOD FOR DETERMINING THE PRESENCE OF KNOTS OR VOIDS IN WOOD

The U.S. Government may have rights in this patent application and the invention disclosed and claimed herein by reason of Contract No. 92-34158-7183, Wood Utilization Special Research Grant.

BACKGROUND OF THE INVENTION

1. Field of the Invention

The invention disclosed and claimed in this application pertains to a method for determining the presence and location of knots or voids in lumber. Specifically, an infrared imaging system is provided which permits the preparation of digital information regarding the thermal profile of heated lumber surfaces, which in turn indicates the presence, and locations, of knots and/or voids in the surface of the lumber so heated. This information may be used to control for wood quality, to program lumber saws or treatment apparatus and operations, etc.

2. Background of the Prior Art

Efforts to improve and automate processes for grading, trimming, and cutup of softwood and hardwood lumber by non-contact, non-labor intensive methods are being widely pursued. Defect detection by non-contact means will allow automated grading, sawing to remove selected defects, and/or other production treatments. Detection of the presence of knots is especially important as knots are the most numerous of the defect types. Voids are also an important defect type that occur in the form of rot, worm or grub holes, and unsound knots that have fallen out.

Existing technology for defect detection has focused largely on the use of CCD scanners or cameras. U.S. Pat. No. 4,827,142, Hatje, is representative of such systems. One obstacle presented in connection with the use of cameras of this type has been the difficulty encountered in differentiating knots from clear wood. Some tree species have dark knots and light colored clear wood that makes knot detection relatively easy. Other species, however, such as the oaks, cherry, basswood, western red cedar, walnut, and others have knots that are nearly the same color as the surrounding clear wood. This difficulty has lead to the use of X-ray devices to detect knots in conjunction with CCD cameras that detect other defect types. See, e.g., International Patent WO 90/11488, Flatman et at, as an example of a system of this type. This reference focuses on real time computer control of the process, which permits programmed control over the lumber edging process.

Other attempts to address the problem caused by the lack of adequate color contrast in CCD cameras are reflected in the use of scanning cameras generating separate colored images of the lumber, the distribution of color intensity for each color being analyzed to detect dark defects such as knots, as reflected in U.S. Pat. No. 4,992,949 Arden. There is no indication that this device solves the knot detection problem for species with knots that are nearly the same color as the clear wood surrounding them.

An additional problem with CCD camera detection of knots as dark objects, aside from inability to detect knots in species without contrasting dark knots and light clear wood, is that stray dark marks are often imparted to the wood surface during manufacturing. Marks from oxidized steel often occur as a result of saws rubbing on the wood surface during sawing. Dirt or scuff marks from handling are often dark. Sticker stain leaves a dark linear mark perpendicular to lumber linear axis. Each of these dark marks as well as others present from various causes may be mistaken by CCD cameras for dark knots.

Voids are generally easy for CCD cameras to detect down to a very small size. However, very small knots of less than ⅛-inch diameter are difficult for this technology to detect.

Several processes have been developed using laser irradiation and photo sensors to determine the presence of knots or other features in lumber being inspected. Thus, U.S. Pat. No. 3,976,384, Matthews et al, U.S. Pat. No. 4,831,545, Floyd et al and U.S. Pat. No. 4,916,629, Bogue et al, are all directed to electro-optical scanning systems wherein laser illumination is used to determine grain angle. The location of knots are inferred by the high grain angles that nearly always surround them. These technologies are relatively expensive to implement and no commercial installations of devices based on these principles have been reported.

In industries unrelated to the wood products industry, heat profiles, as determined by infrared cameras, have been used for the inspection of various products. U.S. Pat. No. 4,118,732, Ichijima et al, describes a process for using variable temperature images caused by flaws on the surfaces of inspected articles to identify the flaws and permit corrective measures. The patent is directed to heated metal products. An infrared camera and detector is used to observe moving targets or items, in U.S. Pat. No. 4,724,482, Duvent, particularly suitable for the detection of intruders and various other moving targets. This system converts the observed thermal image, coupled with an electronic digital signal processor, and means for visualization of the signal.

U.S. Pat. No. 4,771,468, Batchelder et al, provides a method for inspecting integrated circuits, which employs a video camera, the video signal from which is first digitized by a high-speed analog digital converter and frame grabber. This is particularly illustrated in FIG. 8, and described at column 7, line 45–column 8, line 30. In this method, the digital information is communicated to a microcomputer or PC, which permits identification of flawed elements. Another system which uses a camera image connected with a frame grabber in turn connects with a computer to measure and digitalize image information as described in SIR H 999, Merkel et al.

A representative system for determining moving objects such as intruders is described in U.S. Pat. No. 5,059,796, Nakamura, which employs an infrared camera, the analog image signal of which is inputted to a write controller, which converts the received image into a digital signal, written into frame units for a frame grabber. Differences in temperature are compared, to determine the shape of the unknown trespasser. Thus, this process, applied to living individuals, uses the infrared camera input to compare, frame-by-frame, the analog signal obtained with the adjacent analog signal, to determine temperature variations.

Thus, other industries have developed surface inspection methods which permit the use of infrared camera images, the analog information from which is converted to a digital signal, connected with a computer, which is employed to localize and identify various surface flaws or modifications.

It remains an object of the wood products industry to provide an automated or substantially automated system for the improved detection of knots on lumber surfaces, coupled with the ability to use that information to control subsequent processing, such as grading, sawing, or other processing needs by a method which provides the speed and reliability of processes applied to heat-yielding objects of the type described above.

SUMMARY OF THE INVENTION

The above objects, and others, are achieved by a method which involves heating wood by some method. The method may be by heated platen, forced hot air, infrared heater, microwave, convection oven, laser, or some other means. Subsequent movement of the heated wood past an infrared imaging camera allows knots and voids in the wood surface to be detected based on the localized knot or void temperature being different from that of the surrounding wood. An infrared camera scans the surface of the wood as it passes beneath it. A data acquisition device converts the analog signal to a digital signal. The heat distribution of the wood surface is transmitted to a computer where the values are compared to locate areas with temperature differences. This information on defect location can be used for grading purposes, to control a sawing apparatus for the purpose of cutting up the scanned wood, or for processing the wood for any other purpose.

DETAILED DESCRIPTION OF THE INVENTION

Figure 1:
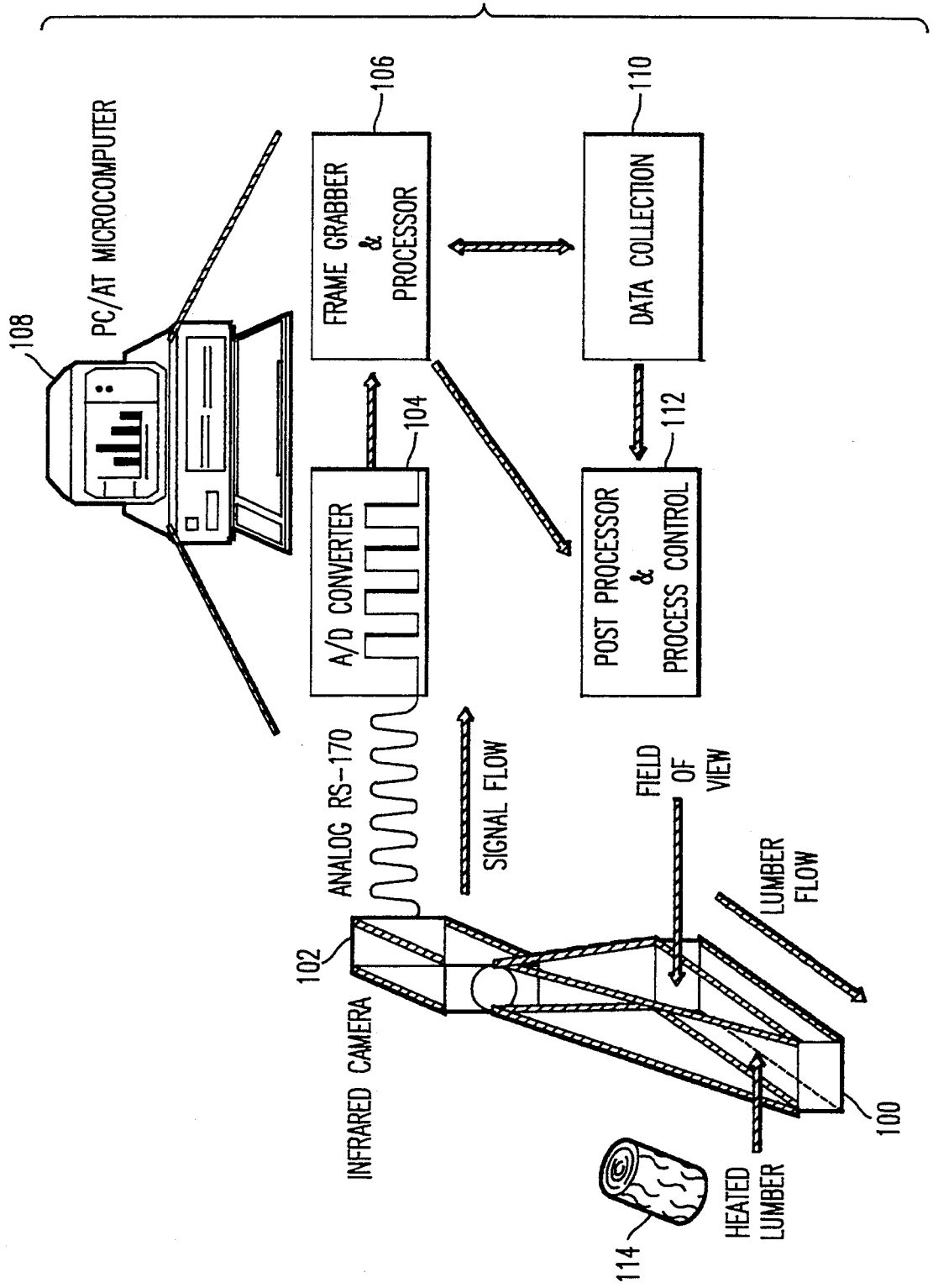
FIG. 1 is a schematic illustration of the infrared detection system of the invention for the detection of knots and voids in lumber surfaces.

The inventive method for detecting knots and voids on the surface of wood employs an infrared imaging system. Thus, wood in any form, that is, in veneer, lumber, raw wood, or any other form, is heated by any means for heating the wood, which may include heated platen, forced hot air, infrared heater, microwave, oven, laser, or other means. Preferably, the wood is heated by infrared irradiation. Using infrared irradiation means 114 illustrated in the Figure, the heated lumber is moved to a location within the field of view of an infrared camera 102. The infrared camera may be either a field view camera or a line-scan camera. The lumber 100 may either be held stationary within the field of view for a sufficient time to obtain a complete infrared image, or may be moved continuously past the field of view depending on whether the camera is still or scanning. This infrared image is fed, through a data acquisition system of the type described in the references mentioned above, to an analog/digital converter 104, wherein the analog image is converted to a digital signal. This digital information is processed in a frame grabber and processor, the processed data being stored in a data collection unit. The necessary hardware and software for conversion, storage and inspection, may be in the form of a dedicated microcomputer, or other computing means such as a PC 108. Analog/digital converter 104 and frame grabber and processor 106 may be of the type described above in connection with scanning systems for unrelated materials. The data collection unit 110 is generally a microprocessor, which, through the use of microcomputer or PC 108, may be used for control of post-imaging procedures via post processor 112. Thus, the information obtained on knot and void location can be used alone, or in combination with defect data obtained from other sensors, to allow for the grading of lumber, for identifying specific pieces for specific uses, or fields of use. Additionally, this information can be used to control downstream means for sawing or other manipulation of the wood.

It is noted that when wood is heated uniformly the knot defects are detected based on their being a different temperature than the surrounding wood. The knot temperature difference may be either cooler or hotter than the surrounding wood depending on the time lag between the heating step and the infrared camera scanning step. Experiments have shown that knots both absorb and give off heat more slowly than clear wood. If infrared scanning occurs immediately after heating, the knots will be cooler that the surrounding clear wood. If a short cooling off period is allowed, the knots will be hotter than the surrounding clear wood. Species of wood will vary with respect to the time periods required to obtain cool versus hot knots. However, this phenomenon has been observed for all species tested.

Large voids in the wood will also be of different temperature than the surrounding clear wood. Voids, however, respond differently to heating based on their size. Large voids will always be cooler than the surrounding clear wood. Small voids such as small grub holes will be cooler than the surrounding wood immediately after heating. However, these small holes will accumulate heat from the surrounding wood, and after a short period of time will be hotter than the surrounding wood. Therefore, voids may also be detected as hotter or cooler areas on the wood surface.

The individual elements of the apparatus used to effectuate the system are not novel, per se. System software has been written specifically for the detection system, and subsequent control. Commercially available software is currently available for analog/digital conversion, frame grabbers and processors, and data collection and comparison, as noted above. Such conventional apparatus and software can be adapted for this system, without inventive effort.

This invention has been described with reference to a generic system, as well as specific embodiments. Modifications, particularly in the form of specialized equipment, and additional processing steps, will occur to those of ordinary skill in the art without the exercise of inventive faculty. Such modifications remain within the scope of the invention, save as excluded by the claims presented below.

What is claimed is:

1. A method for detecting knots and voids in solid wood, comprising:
   uniformly heating said wood,
   obtaining an infrared image of said heated wood,
   inspecting said image to determine locations in said wood wherein the temperature is different from the remainder of said wood, wherein said locations reflecting a temperature different from that of the remainder of said wood correspond to a knot or void in said wood.

2. The method of claim 1, wherein said image is obtained from an infrared camera, and said image is inspected by converting said image to a digital signal, the signal being inspected by computing means to determine the locations that correspond to a knot or void in said wood.

3. The method of claim 1, wherein said wood is heated by infrared heater.

4. The method of claim 1, wherein the locations corresponding to a knot or void are communicated to a processing means for controlling physical manipulation of said wood.

5. The process of claim 4, wherein said processing means includes sawing means, said processing means controlling said sawing means to physically exclude said locations exhibiting a temperature different from the remainder of said wood.

6. The method of claim 4, wherein said processing means includes means for grading or sorting of said wood.

* * * * *